(12) United States Patent
Greiner-Perth et al.

(10) Patent No.: US 11,844,723 B2
(45) Date of Patent: Dec. 19, 2023

(54) DISPENSER FOR DISCHARGING PHARMACEUTICAL LIQUIDS

(71) Applicant: Aptar Radolfzell GmbH, Radolfzell (DE)

(72) Inventors: Jürgen Greiner-Perth, Gottmadingen (DE); Gerald Krampen, Radolfzell (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 155 days.

(21) Appl. No.: 17/605,433

(22) PCT Filed: Apr. 16, 2020

(86) PCT No.: PCT/EP2020/060740
§ 371 (c)(1),
(2) Date: Oct. 21, 2021

(87) PCT Pub. No.: WO2020/216673
PCT Pub. Date: Oct. 29, 2020

(65) Prior Publication Data
US 2022/0192872 A1 Jun. 23, 2022

(30) Foreign Application Priority Data
Apr. 26, 2019 (EP) .................................. 19171385

(51) Int. Cl.
*A61F 9/00* (2006.01)
*B05B 11/00* (2023.01)
(Continued)

(52) U.S. Cl.
CPC .......... *A61F 9/0008* (2013.01); *A61M 31/00* (2013.01); *B05B 11/0032* (2013.01);
(Continued)

(58) Field of Classification Search
CPC .......... A61F 9/00; A61F 9/008; A61M 31/00; A61M 2210/0618; A61M 2210/0662;
(Continued)

(56) References Cited

U.S. PATENT DOCUMENTS 2,884,164 A 4/1959 Kleid
3,161,329 A 12/1964 Fedit et al.
(Continued)

FOREIGN PATENT DOCUMENTS

DE 1907358 9/1969
DE 1491706 2/1970
(Continued)

OTHER PUBLICATIONS

International Search Report with English Translation issued in corresponding International Application No. PCT/EP2020/060740 dated Oct. 14, 2020 (10 pages).
(Continued)

*Primary Examiner* — Lien M Ngo
(74) *Attorney, Agent, or Firm* — FLYNN THIEL, P.C.

(57) ABSTRACT

A dispenser for discharging pharmaceutical liquids in the form of individual drops, having a liquid store, a pump device with a pump chamber with a variable volume, and a dispensing opening. The dispenser additionally has a membrane part which delimits the pump chamber on one side and which changes the volume of the pump chamber by moving and/or deforming. The dispenser has a housing, within which the pump device is provided, and an actuation button movable relative to the housing between a non-actuated starting position and an actuated end position to move or deform the membrane part and to decrease the size of the pump chamber to discharge the liquid. The membrane part is secured to the housing and to the actuation button. The
(Continued)

pump chamber achieves a high degree of compression and a toggle switch is used as the actuation button.

17 Claims, 7 Drawing Sheets

(51) Int. Cl.
*A61M 31/00* (2006.01)
*B05B 11/10* (2023.01)

(52) U.S. Cl.
CPC .... *B05B 11/0067* (2013.01); *B05B 11/00444* (2018.08); *B05B 11/103* (2023.01); *B05B 11/1064* (2023.01); *B05B 11/1074* (2023.01); *A61M 2205/3337* (2013.01); *A61M 2210/0618* (2013.01); *A61M 2210/0662* (2013.01)

(58) Field of Classification Search
CPC .......... B05B 11/0032; B05B 11/00444; B05B 11/0067; B05B 11/103; B05B 11/1064; B05B 11/1074; B05B 11/1061; A61J 1/2003; A61J 1/2051
USPC ..... 222/401, 420, 422, 321.8, 209, 213, 214
See application file for complete search history.

(56) References Cited

U.S. PATENT DOCUMENTS

| | | | |
|---|---|---|---|
| 3,452,905 A | 7/1969 | Micallef | |
| 4,216,882 A * | 8/1980 | Basile | B05B 11/1035 222/207 |
| 4,949,876 A | 8/1990 | Schneider | |
| 5,454,488 A * | 10/1995 | Geier | B05B 11/103 222/380 |
| 6,000,580 A * | 12/1999 | Nilson | A61M 15/0025 222/562 |
| 3,006,870 A1 | 8/2011 | Stadelhofer et al. | |
| 8,292,129 B2 * | 10/2012 | Stadelhofer | B05B 11/0027 222/207 |
| 9,073,080 B2 * | 7/2015 | Wochele | B05B 11/1004 |
| 9,241,828 B2 * | 1/2016 | Pardes | A61F 9/0017 |
| 2007/0210114 A1 * | 9/2007 | Stadelhofer | B05B 11/106 222/335 |
| 2010/0187261 A1 * | 7/2010 | Wochele | B05B 11/1016 222/207 |
| 2010/0219207 A1 * | 9/2010 | Canfield | B05B 11/1033 222/207 |

FOREIGN PATENT DOCUMENTS

| | | |
|---|---|---|
| DE | 68903116 T2 | 2/1993 |
| DE | 4141825 A1 | 6/1993 |
| DE | 102006012898 A1 | 9/2007 |
| EP | 0784513 B1 | 7/1997 |
| FR | 1531558 | 7/1968 |
| FR | 2877325 A1 | 5/2006 |
| JP | 2007245145 A | 9/2007 |
| JP | 201292850 A | 5/2012 |
| WO | 2004062422 A1 | 7/2004 |
| WO | 2013057223 A1 | 4/2013 |

OTHER PUBLICATIONS

Written Opinion of International Searching Authority issued in corresponding International Application No. PCT/EP2020/060740 dated Oct. 14, 2020 (14 pages).

Japanese Office Action with English translation issued in corresponding Japanese Application No. 2021-557016 dated Aug. 26, 2022 (14 pages).

* cited by examiner

DISPENSER FOR DISCHARGING PHARMACEUTICAL LIQUIDS

FIELD OF THE INVENTION

The invention relates to a dispenser for discharge of pharmaceutical liquids, especially for the dropwise discharge of pharmaceutical liquids in the form of individual droplets. The droplets may be for example eye drops, ear drops or nose drops.

A dispenser of the generic type has a liquid reservoir, a pump device having a volumetrically variable pump chamber, and a delivery opening for delivery of the liquid. For variation of the volume of the pump chamber for the purpose of sucking in liquid from the liquid reservoir and for pressurization of the liquid for the purpose of discharge, the pump chamber is bounded on one side by a membrane part that consists at least partly of a soft plastic and hence is displaceable with simultaneous deformation. A dispenser of the generic type also has a housing within which the pump device is provided. An actuating button displaceable with respect to the housing between an unactuated starting position and an actuated final position is provided for displacement/deformation of the membrane part for the purpose of liquid discharge.

BACKGROUND OF THE INVENTION

Figure 2A:
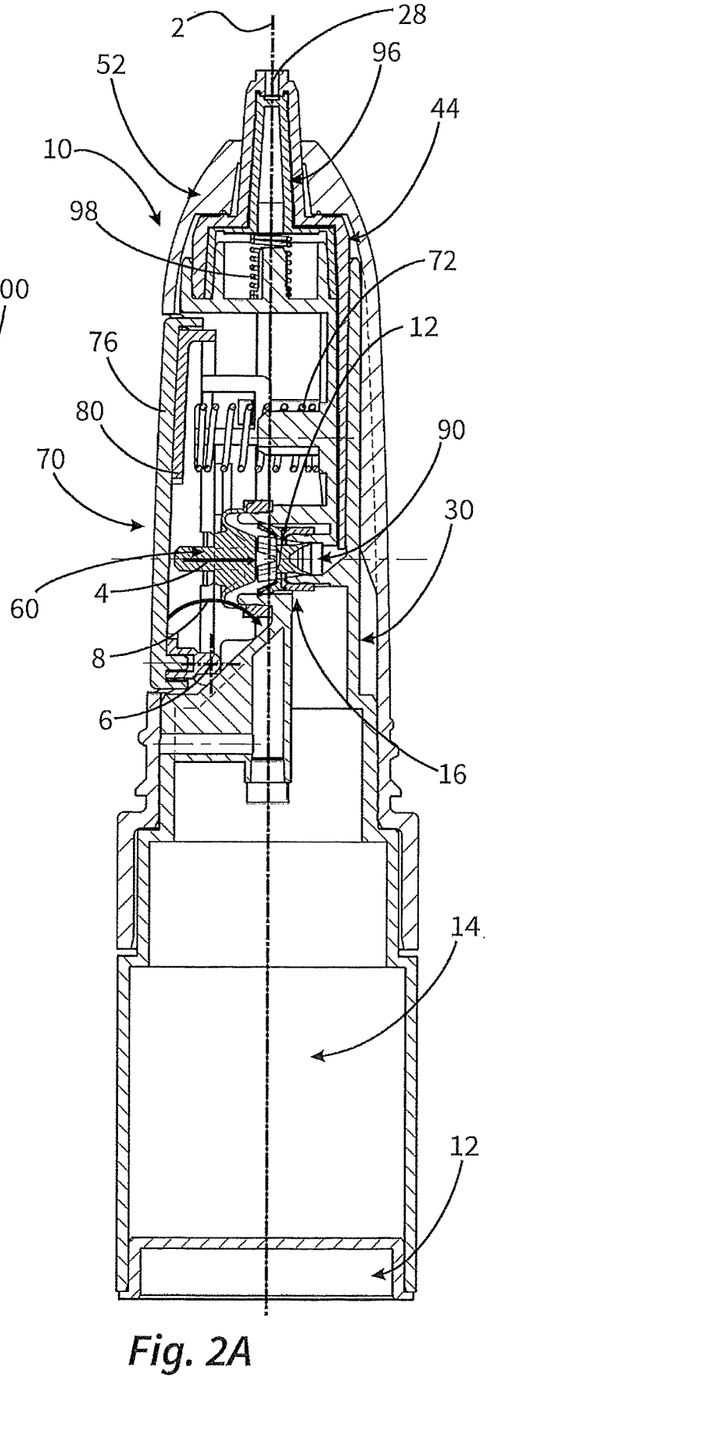
FIGS. 2A and 2B show the dispenser in a cross-sectional diagram together with the internal pump chamber which is bounded by a membrane part and a valve component.

DE 102006012898 A1 in FIGS. 2a and 3b discloses a droplet dispenser having a pump device, the pump chamber of which is bounded by a membrane part on one side. However, some aspects of the dispenser described therein are disadvantageous. In particular, the handling of the soft membrane part before and in the course of assembly and the coupling of the actuating button and the membrane part to one another during assembly are problematic in the implementation of automated assembly. Furthermore, the configurations known from the prior art present problems in first use, since the arrangement and configuration of the valves and of the volumes of the channels and of the pump chamber make it difficult to initially drive out the air.

OBJECT AND ACHIEVEMENT

It is an object of the invention to develop a dispenser of the generic type as described that has a pump chamber bounded by a membrane part in that the disadvantages described are overcome or at least reduced.

The object is achieved by proposing a dispenser having a liquid reservoir for storing the liquid prior to discharge, a housing having an integrated pump device with a volumetrically variable pump chamber, and a delivery opening for delivery of the liquid. The pump device serves the purpose of sucking in liquid from the liquid reservoir and delivering the liquid through the delivery opening on actuation of the dispenser.

The pump chamber is closed on one side by the membrane part that is inherently deformable at least in sections and comprises a soft and hence readily deformable plastic at least in the region of a pump chamber wall. Other wall portions of the pump chamber are formed by rigid housing sections bonded tightly to the membrane part. The membrane part can be depressed in the direction of the pump chamber in order to reduce the volume of the pump chamber and hence to push liquid in the direction of the delivery opening. Typically, the pump chamber is bounded by two valves: on the inlet side by an inlet valve that opens in the event of a reduced pressure in the pump chamber relative to the liquid reservoir, and on the outlet side by an outlet valve that opens at a positive pressure in the pump chamber compared to a delivery channel that leads to the delivery opening. The inlet valve is closed at identical pressure in the liquid reservoir and in the pump chamber, and preferably opens over and above a reduced pressure of about 0.1 to 0.2 bar in the pump chamber. The outlet valve is closed at identical pressure in the pump chamber and the connecting delivery channel, and preferably opens over and above a positive pressure of about 0.5 bar in the pump chamber. A further valve that opens in the case of a positive pressure of the liquid in the delivery channel relative to an ambient pressure is preferably upstream of the delivery opening. This delivery valve is preferably designed to open at a positive pressure of at least 0.3 bar, preferably at least 0.5 bar. The positive pressure to open the valve, in the case of pharmaceutical liquids without preservatives, should not be too low in order as far as possible to prevent external fluctuations in pressure from causing opening. In the case of liquids with preservatives, the requirements are lower. It may also be the case here that opening pressures of the delivery valve of down to 0.05 bar are possible and advantageous.

For actuation of the pump device, the dispenser has an actuating button displaceable between an unactuated starting position and an actuated final position, the displacement of which to the final position leads to displacement/deformation of the membrane part and hence to a reduction in the size of the pump chamber for the purpose of liquid discharge.

Although it is not absolutely necessary for the aspects of the invention described hereinafter, the implementation of the measures described is considered to be advantageous especially in the case of what is called a side-actuation dispenser. In such a side-actuation dispenser, the housing of the dispenser has an elongate outer shape aligned in the direction of a main direction of extension, with the delivery opening provided at the distal end of the dispenser. The housing may have an essentially round cross section, but may also vary therefrom and have more of a flat design. The actuating button is provided at the side of the housing of the dispenser and can be depressed in the direction of a central axis in order thereby to deform the membrane part to reduce the size of the pump chamber for the purpose of liquid discharge. The actuating button is typically actuated by a thumb. The actuating button is preferably disposed in an aperture in the housing, especially recessed relative to the surrounding housing sections, flush therewith in a rest position, or protruding outward from the housing by only a few mm, especially less than 5 mm.

The aspects of the invention described hereinafter are advantageous especially in the case of implementation of a droplet dispenser, i.e., a dispenser intended to deliver pharmaceutical liquid in the form of single droplets. For this purpose, a droplet formation structure is preferably provided beyond the delivery opening, i.e., a region in which the liquid delivered collects until the volume thereof is sufficient to form a droplet which becomes detached from the droplet formation structure under gravity. More particularly, the droplet formation structure may be a droplet formation surface surrounding the delivery opening, which especially has a flat or concave shape and/or is bounded on the outside by a sharp break-off edge with a radius of curvature of preferably less than 0.5 mm.

If a dispenser of the invention is configured as a droplet dispenser, the pump chamber preferably has a utilizable volume formed by the volume differential between maximum volume and minimum volume of the pump chamber of between 20 µl and 50 µl, preferably between 30 µl and 40 µl. Such a volume corresponds roughly to the volume of a droplet formed from customary configurations of the droplet formation structure. The user is thus able to deliver exactly one droplet by one actuation of the actuating button. If the droplet formation structure is designed to form larger droplets, the utilizable volume of the pump chamber is preferably correspondingly greater. Even in the case of configuration of the dispenser as a droplet dispenser, a larger pump chamber may be appropriate in order to be able to deliver several droplets with one actuation.

In order to be able to push out the air present in the pump chamber on first use in spite of a comparatively low pump chamber volume, an outlet valve of the pump chamber is preferably designed to open at only a low positive pressure. In particular, however, it is advantageous for problem-free first use of the dispenser when the quotient between a minimum pump chamber volume and a maximum pump chamber volume is not more than 1:2, preferably not more than 1:3. Such a quotient can especially be achieved by the measures of the invention elucidated below.

In a first aspect of the invention, the actuating button mentioned has a button component made of a rigid plastic. In addition, the dispenser has a spring device by which the actuating button is subjected to a force in the direction of the unactuated starting position, such that the actuating button is pushed back into the starting position after the actuating button has been pressed.

The membrane part that bounds the pump chamber is connected to the button component mentioned in the actuating button such that the actuating button also moves the membrane part in the displacement to the starting position thereof brought about by the spring device. The membrane part may thus be manufactured from a plastic that does not have any strong inherent tendency to reset, but is pulled back indirectly by the return spring. The connection between the soft and deformable plastic of the membrane component and the plastic of the button component that is harder and more rigid by comparison is implemented by having a connecting section of the membrane part being clamped between at least two clamp surfaces of the button component.

It has been found that the technique of clamping is of good suitability for transmitting tensile forces from the button component to the membrane part and of comparatively good implementability in an automated assembly. For this purpose, the two clamp surfaces may be pushed apart during assembly, for example by a kind of spreader, such that a section of the membrane component can be introduced between the at least two clamp surfaces, and then the spreader is pulled out. The clamp surfaces then adjoin the section of the membrane part that has been pushed in on either side, leaving regions on each side between the clamp surfaces with respect to the circumference of the connecting section in which the button component is not in contact with the connecting section. The connecting section is a one-piece portion of the membrane part that preferably forms a projecting section that can thus be made to engage efficiently with the clamp surfaces.

Even though two clamp surfaces are typically considered to be sufficient, it is also possible to use more clamp surfaces. For example, three or more clamp surfaces that project toward one another in a star shape are also an appropriate design.

The clamp surfaces may be flat. In order to further increase the transmissible tensile forces, it may alternatively be advisable to provide each of the clamp surfaces with a sharp-edged penetration geometry having a radius of curvature of less than 0.3 mm at the sharp edge, which can correspondingly penetrate deeper into the inserted section of the membrane part, hence increasing the clamping effect.

In a preferred configuration, the button component has a coupling aperture in the form of an elongate aperture, at the edge of which the two clamp surfaces are provided opposite one another. Such an elongate aperture, in the direction of a longitudinal extent, is then preferably larger by at least a factor of 2 or 3 than the distance between the mutually facing clamp surfaces. The elongate extent facilitates the widening in the assembly for the purpose of inserting the membrane part.

It is also especially advantageous when at least one assembly aperture in the form of an elongate aperture is provided parallel to the coupling aperture in the button component. Such an assembly aperture is preferably provided on either side of the coupling aperture. The at least one coupling aperture, during assembly, enables deflection of at least one clamp surface for the purpose of inserting the connecting section of the membrane part without needing to significantly deform and potentially damage the plastic of the button component.

In a second aspect of the invention, the dispenser has an opposing wall on an opposite side of the pump chamber from the membrane part. This is preferably formed from a rigid component. A valve component is inserted into this opposing wall. The valve component has at least one valve surface of an inlet valve or an outlet valve of the pump device, with this valve surface preferably being designed to adjoin a surface of the housing component of the opposing wall in the closed state of the valve. It is especially advantageous when the valve component has valve surfaces both of the inlet valve and of the outlet valve, preference being given here to a design in which an inlet channel into the pump chamber and an outlet channel into the pump chamber are in a mutually concentric arrangement, such that a single valve component is disposed at a wall between the inlet channel and the outlet channel and has both one valve lip facing inward and one facing outward.

In this aspect of the invention, the membrane part is displaceable in the course of actuation such that, in an actuated final position, the membrane part adjoins the valve component at least in sections, especially adjoining a valve surface in the form of a valve lip made of elastic plastic at least in sections.

Such displaceability of the membrane part as far as the opposite valve component enables a very low minimum volume of the pump chamber. In the final position of the membrane part, the membrane part reduces the distance between membrane part and valve component to zero at least in sections. It is especially advantageous when surfaces made of readily deformable plastic of the membrane part and of the valve component come to rest against one another, since these have a particularly good fit to one another and hence further promote reduction in the minimum volume. In a particular configuration, it may additionally be the case that the membrane part in the final position thereof is pushed onto the valve component in such a way that the inlet valve or outlet valve is forcibly opened mechanically in order to allow compressed air present in the pump chamber to escape.

The membrane part preferably has a middle portion that projects into the pump chamber and has a shape adapted to the shape of the valve component, it being preferable that the middle portion has a shape that narrows in the direction of the valve component and the valve component has a complementary goblet-like shape defined by an inlet valve lip, into which the middle portion meshes. This configuration too promotes reduction of the minimum volume of the pump chamber.

In addition, the membrane part can have a ring surface surrounding the middle portion of the membrane part. The ring surface is effectively turned over in the event of a deformation of the membrane part during the reduction in size of the pump chamber. As a result, a ring region of the ring surface that points outward in the starting state points inward in the final position of the membrane part that results from actuation. The turning-over or rolling-off makes it possible to keep the minimum pump chamber volume low since the pump chamber wall formed by the membrane part in the unrolled state can adjoin a rigid outer wall of the pump chamber in a flush manner.

In a third aspect of the invention, the membrane part is secured circumferentially to a housing section of the housing in an outer edge region. For securing of the edge region of the membrane part to the housing section, a securing ring made of a rigid plastic is provided here, with a rigid plastic being understood to mean a plastic having a greater modulus of elasticity than the modulus of elasticity of the membrane part in the region of the pump chamber wall which is deformed in the case of reduction in the pump chamber size.

The securing ring may take the form of a component separated from the membrane part, which comes into contact with the membrane part only during assembly and presses the membrane part against the housing section mentioned with sealing, or itself presses against and provides sealing with the housing section.

Preference is given, however, to a one-piece configuration in which the membrane part comprises different plastics joined directly to one another by multicomponent injection molding. The softer plastic mentioned here forms the material for the parts to be deformed as intended during actuation, especially for the ring region in the membrane part. The more rigid component by comparison forms a circumferential region shaped thereon, which thus forms the securing ring.

In the assembled state, the securing ring ensures that the edge of the membrane part is reliably fixed to the housing section. This is advantageous especially when particularly soft plastic is chosen for the sections of the membrane part to be deformed as intended in operation, since such a material is not of good suitability for fixing to the housing without an additional securing ring.

If the securing ring is a one-piece portion of the membrane part, this additionally considerably simplifies the handling of this component during assembly. The rigid portion of the membrane part formed by the securing ring, proceeding from the membrane parts supplied in an undirected manner, facilitates individualization and alignment for the subsequent assembly.

The housing section to which the membrane part is fixed by the securing ring is preferably a ring-shaped housing section, with the securing ring clamped to an outer face of the annular housing section and with an inner face of the housing section forming a circumferential wall of the pump chamber.

In a fourth aspect of the invention, the actuating button is designed as a rocker button designed to be rockable with respect to the housing about a rocker axis. The rocker button here has a rigid button component that presses against the membrane part in the case of rocking movement of the actuating button and hence reduces the size of the pump chamber. There is preferably direct touch contact and hence functional contact between the button component rockable about the rocker axis and the deformable membrane component.

The use of a rocker button permits quite exact dosage. This is associated in particular with the fact that the rocker button, by virtue of the pivot linkage, does not have a tendency to twist or the like, and that the user, via the distance of the manual application of force from the rocker axis, has good controllability of the speed at which the rocker button is depressed. This may especially be advantageous in the case of droplet delivery since the rocker button can have an exact influence on the juncture of detachment of the droplet from the droplet formation structure.

The use of a rocker button is especially appropriate in the context of the membrane part provided in accordance with the invention since the membrane part, by virtue of deformability thereof, is of good suitability for converting a rocking motion of a rocker button to an essentially linear movement of the displaceable pump chamber wall. It is also very simple for manufacturing purposes to form the membrane part with an elastically deformable compensation section disposed between the pump chamber wall and the rocker button.

The rocker axis of the rocker button is preferably provided at an opposite end of the rocker button from the delivery opening based on the main direction of extension. The rocker axis is preferably aligned orthogonally to the main direction of extension of the dispenser. In principle, such pivot mobility can be achieved by a simple integral hinge. By contrast, however, it is preferable when axis sections that engage with bearings on the respective other side and hence enable rocking mobility are provided on the rocker button or on a surrounding housing section.

As already mentioned above, the dispenser preferably has a spring device that acts on the actuating button and subjects the actuating button to a force in the direction of the unactuated starting position. The spring device may in principle be designed as an elastically deformable spring section in one piece with the actuating button and/or in one piece with the housing. Preference is given, however, to a separate spring device, especially in the form of a helical spring made of plastic or metal. The spring device pushes the actuating button into the unactuated starting position, which increases the size of the pump chamber again and sucks liquid in from the liquid reservoir.

One possible design in principle is one in which the spring device on the one hand and the connection of the rocker button to the membrane part on the other hand are spaced apart identically from the rocker axis. This is the result, for example, when the spring device is configured as a helical spring arranged concentrically around the membrane part for attachment of the membrane part to the rocker button.

However, it is considered to be advantageous when a connecting region by which the rocker button presses against the membrane part and a force input region in which the spring device introduces a reset force into the rocker button are provided on the rocker button at different distances from the rocker axis. It is thus considered to be especially advantageous here when the force input region is further removed from the rocker axis than the connecting region. In addition, it is considered to be advantageous when the distances from the rocker axis differ at least by 20% and are thus significantly different. Different distances of the connecting region and the force input region from the rocker axis have various advantages, especially also simpler assembly since the return spring and the connection to the displaceable pump chamber wall are spatially separated from one another.

Preferably, a dispenser of the invention has a removable dispenser cap which can be placed onto the dispenser housing and removed therefrom for use of the dispenser. The dispenser cap protects the delivery opening when placed on the dispenser. Especially preferably, such a dispenser cap is configured as a ventilated dispenser cap, and for this purpose has at least one ventilation opening by which the delivery opening is connected to a surrounding atmosphere even with the dispenser cap in place. This promotes rapid drying of any residual droplet remaining in situ. As supplied, the ventilation opening is preferably closed and is opened by the user in the course of first utilization. The dispenser cap preferably has a sterile filter that covers the ventilation openings in order to prevent introduction of microbes. In addition, the dispenser cap preferably has an integrated pad which, with the dispenser cap in place, is positioned over or on the delivery opening such that any liquid residue that remains downstream of the delivery opening is absorbed and/or decontaminated thereby.

The liquid reservoir of a dispenser of the invention is preferably provided at the opposite end of the dispenser from the delivery opening. It may be formed by a separate bottle body coupled to, for example screwed onto, the housing surrounding the pump device. In a different configuration, an outer wall of the liquid reservoir is connected to the housing in one-piece form, preferably with a base of the bottle body formed by a separate portion secured to the outer wall. If the liquid reservoir has an invariable volume, the dispenser preferably has a ventilation channel, especially with a sterile filter, via which the liquid reservoir is connected to a surrounding atmosphere. Alternatively, the liquid reservoir may, however, also have a variable internal volume, especially in that a pouch is provided, in which the liquid is stored and which is surrounded by a rigid bottle body. A drawing plunger system also permits the implementation of a variable internal volume.

A dispenser of the invention is intended for use for the discharge of pharmaceutical liquids. Therefore, as supplied, the liquid reservoir is preferably filled with such a pharmaceutical liquid.

In particular, pharmaceutical liquids are those for treatment of elevated intraocular pressure (glaucoma treatment), for treatment of dry eye and for treatment of allergies and inflammations. A particular role is played here by the following groups of molecules: alpha-2 agonists, e.g. brimonidine, prostaglandin analogs (tafluprost, latanoprost, bimatoprost, travoprost), beta-blockers, e.g. timolol, and carboanhydrase inhibitors, e.g. dorzolamide, or hyaluronic acid compounds, film formers, e.g. methylcellulose compounds, and cyclosporine, or antihistamines, e.g. olopatadine and levocabastin, steroids, e.g. loteprednol and dexamethasone, and NSAIDs, e.g. keterolac.

In addition, the dispenser of the invention is advantageously usable for liquids having molecules of one or more of the following types: trichloroacetic acid, trioxysalen, urea, zinc oxide, tacrolimus, clobetasol propionate, mometasone furoate, betamethasone dipropionate, fluocinonide, desoximetasone, triamcinolone acetonide, fluticasone propionate, hydrocortisone, clotrimazole, ketoconazole, miconazole, undecylenoic acid, terbinafine, cyclopirox, tolnaftate, akziklovir, imiquimod, docosanol, finasteride, minoxidil, dexamethasone, tramazoline, naphazoline, nostrilla, oxymethazoline, phenylephrine, phenylpropanolamine, pseudoephedrine, tetryzoline, tramazoline hydrochloride, tuaminoheptane and xylometazoline.

The components of a dispenser of the invention are preferably made from plastic. Only for the springs described and any springs present at the inlet valve and/or the outlet valve does a metallic construction constitute an alternative. The parts intended to be deformable in operation, in particular the predominant portion of the membrane component, the valve lips and the delivery valve body, preferably comprise an elastomer plastic having a modulus of elasticity <200 N/mm². An example of a useful material is an LDPE (low-density polyethylene). The parts that are immobile in operation preferably consist of a plastic having a modulus of elasticity >500 N/mm². This may be, for example, an HDPE (high-density polyethylene) or a PP (polypropylene).

BRIEF DESCRIPTION OF THE DRAWINGS

Further advantages and aspects of the invention are apparent from the claims and from the description that follows of preferred working examples of the invention, which are elucidated hereinafter with reference to the figures.

DETAILED DESCRIPTION OF THE WORKING EXAMPLES

Figures 1A, 1B:
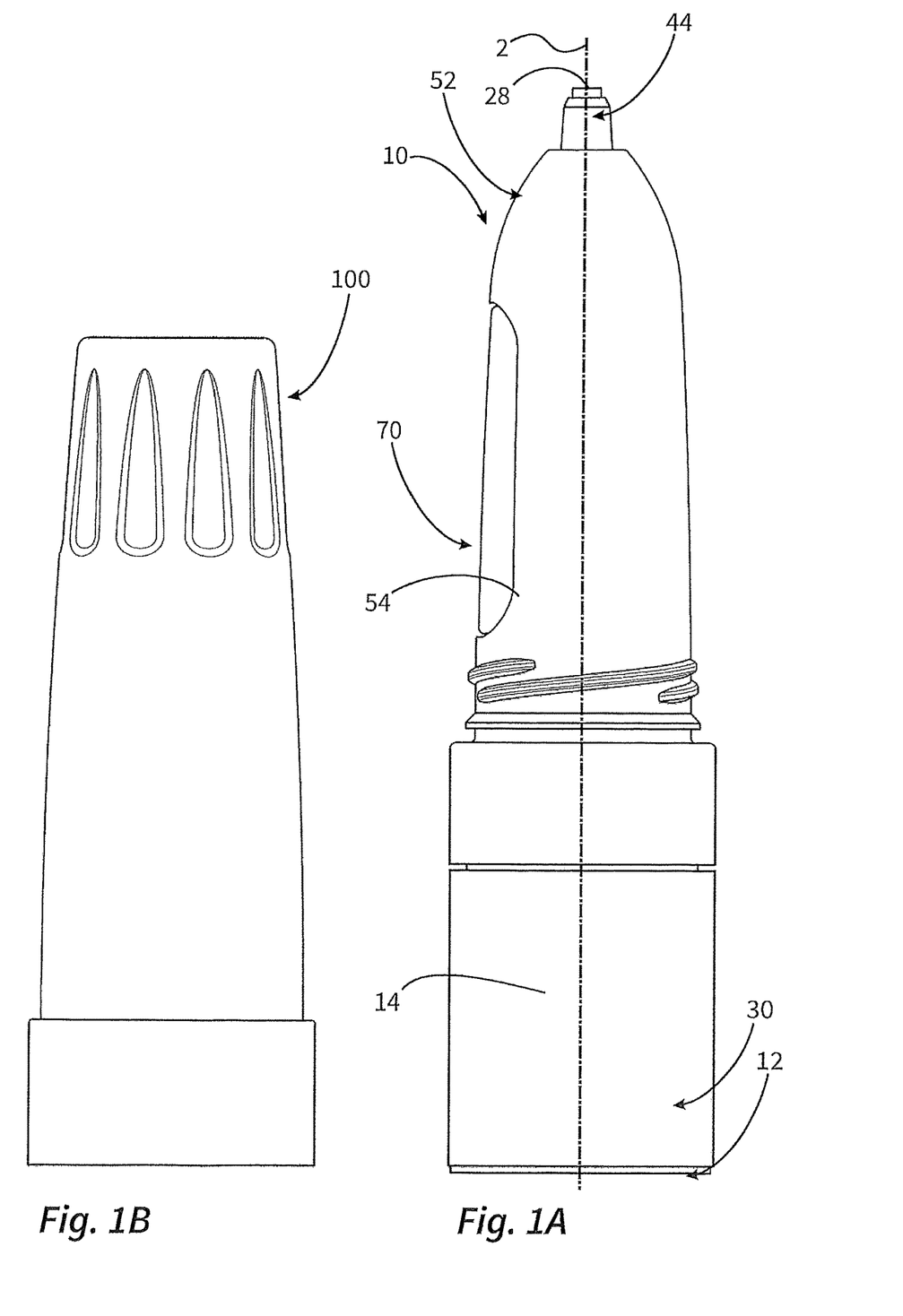
FIGS. 1A and 1B show a dispenser of the invention, comprising a main unit and dispenser cap in a non-sectional diagram.

FIGS. 1A and 1B show a first working example of the dispenser 10 of the invention in a non-section diagram together with a dispenser cap 100. The main unit of this configuration of the dispenser shown in FIG. 1A has an elongate housing composed of various housing constituents 30, 12, 52, 44 and aligned in a main direction of extension 2. As described hereinafter, a pump device 16 is provided within the housing, by which liquid can be conveyed from a liquid reservoir 14 at a proximal end of the dispenser 10 to a delivery opening 28 at a distal end of the dispenser 10. For actuation of the pump device 16, an actuating button 70 is provided.

The dispenser cap 100 shown in FIG. 1B can be threaded onto the housing of the dispenser 10.

Figure 2B:
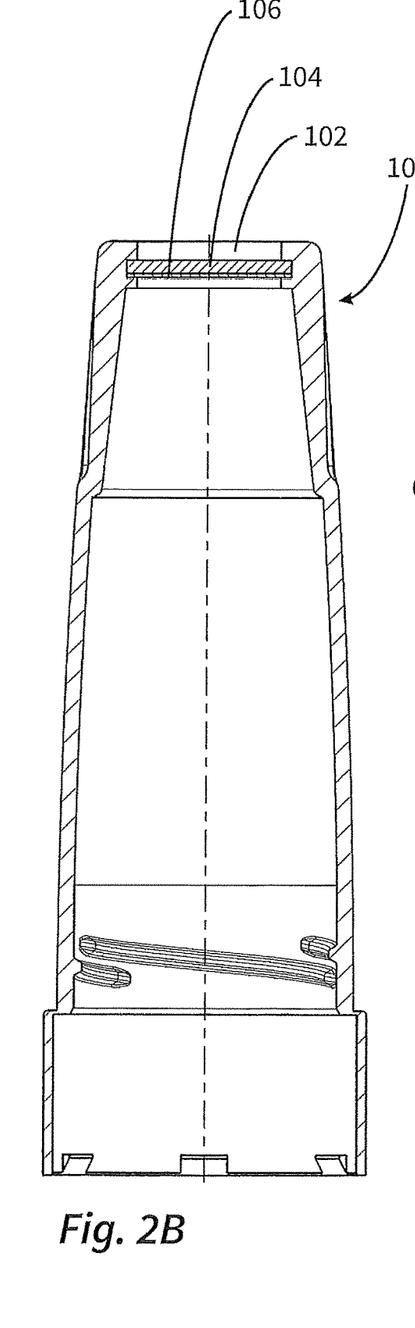

FIGS. 2A and 2B show the main unit of the dispenser 10 and the dispenser cap 100 in a cross-sectional view.

The main elements are to be described first with reference to FIGS. 2A and 2B.

As apparent in FIG. 2A, the main unit of the dispenser 10 comprises multiple housing portions, the first housing component 30 of which is the largest housing component and effectively constitutes a central carrier for further components of the dispenser. The first housing component 30 provides the outer wall of the liquid reservoir 14 at a proximal end thereof. The first housing component 30 is the carrier for various components of the pump device, especially a membrane part 60 and a valve component 90 disposed on opposite sides of a pump chamber 20. The actuating button 70 is hinged to pivot about a rocker axis 6 on the first housing component 30. The actuating button 70 comprises two button components 76, 80, with the inner button component 80 connected to the membrane part 60 in the manner described hereinafter, such that the membrane part 60 can be depressed into the pump chamber 20 by the actuating button 70. A return spring 72 is provided between the button component 80 and the first housing component 30.

A second housing component 44 is joined to the distal end of the first housing component 30. The second housing component 44 is provided at a fixed location on the first housing component 30 and, together therewith, seals off an interior within which a deformable delivery valve body 96 is disposed, to which is in turn assigned a delivery valve spring 98. A further housing component, the outer housing component 52, surrounds the first and second housing components 30, 44, with the second housing component 44 projecting through an aperture 58 in the outer housing component 52 by an applicator tip 46, and with the outer housing component 52 having an aperture 56 in an outer surface 54 through which the actuating button 70 can be depressed in the manner illustrated by the arrow 8, in order thereby to displace the membrane part 60 in the direction illustrated by the arrow 4.

Figures 3, 4:
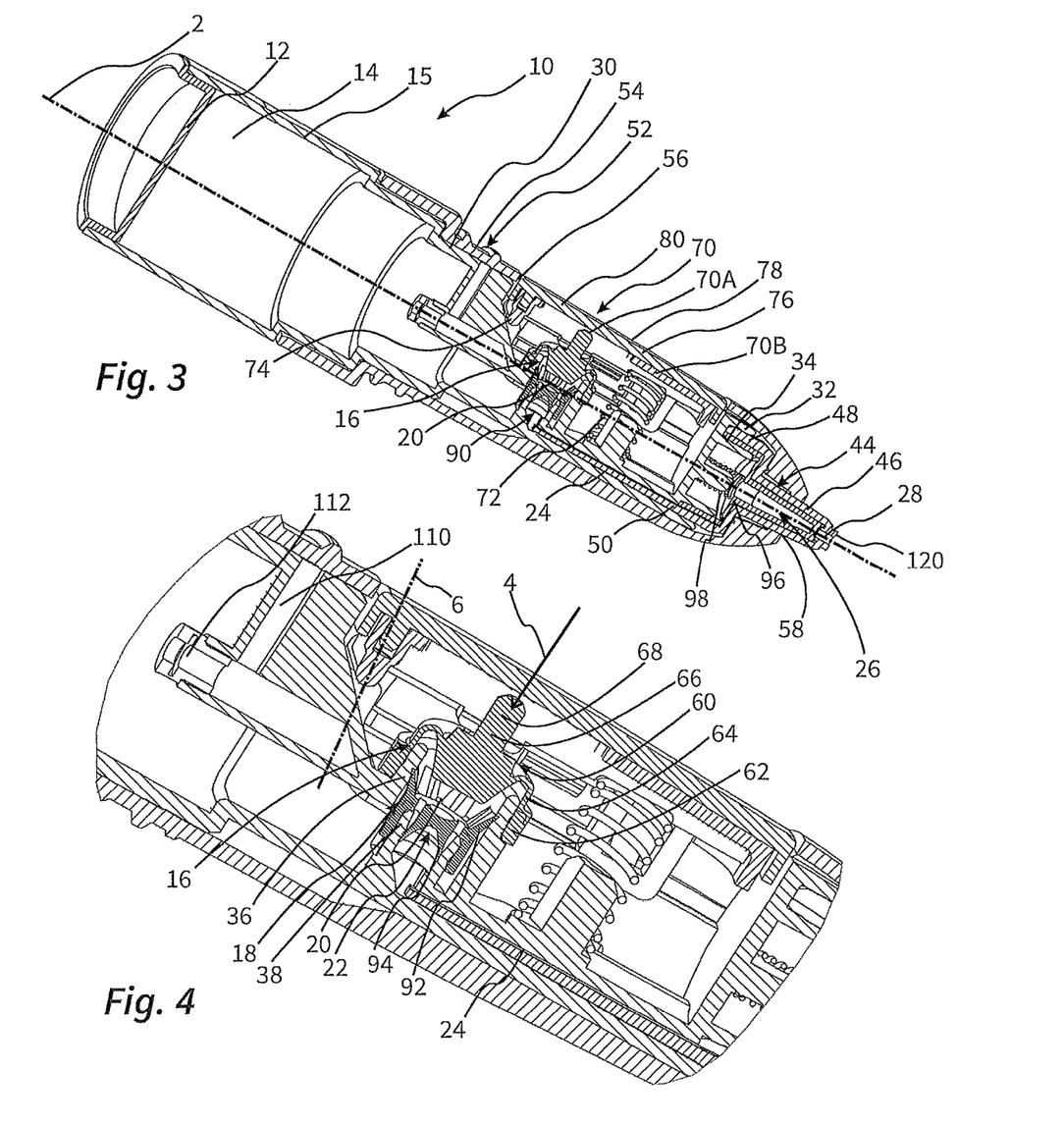
FIGS. 3 and 4 show the dispenser in perspective cross-sectional diagrams.
Figure 8:
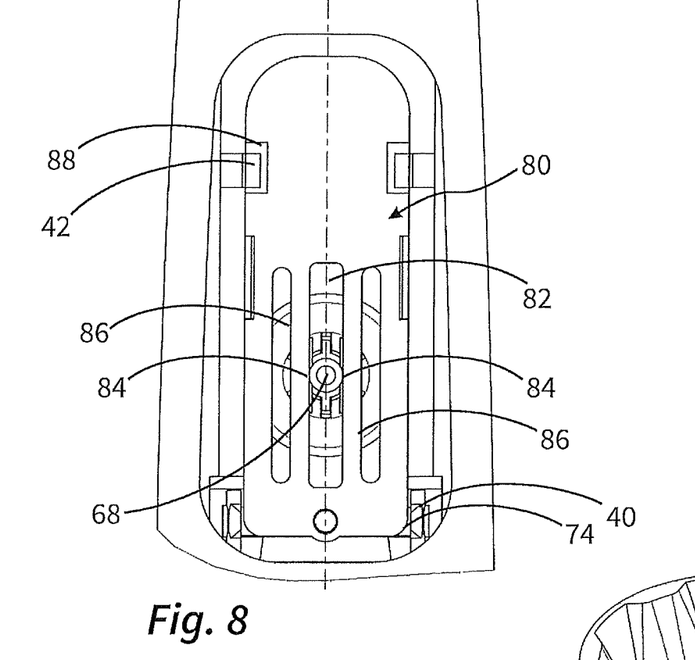
FIG. 8 shows the coupling between the actuating button of the dispenser and the membrane part.
Figure 9:
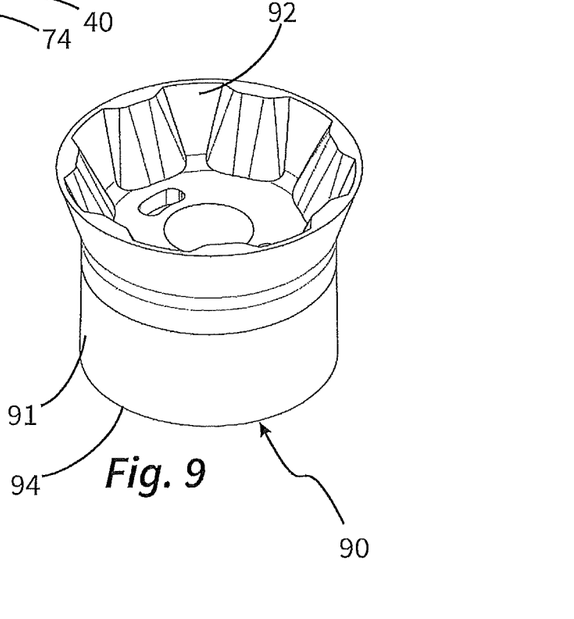
FIGS. 9 and 10 show details of the valve component and the membrane part.
Figure 10:
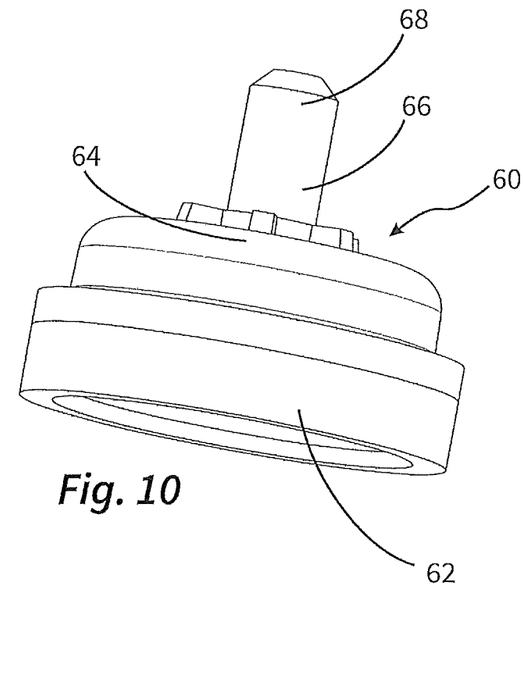

The dispenser is further elucidated by the perspective diagrams of FIGS. 3 and 4 with reference to the details of FIGS. 8 to 10.

Before the discharge of liquid, the liquid is stored in the liquid reservoir 14, which, in the case of the working example of FIGS. 1A to 10, is bounded by an outer surface 15 of the first housing component 30, and which is closed at the proximal end of the dispenser by a snap-in base 12. The dispenser 10 is typically used in an alignment in which the delivery opening 28 points downward, such that the liquid in the liquid reservoir 14 directly adjoins the valve component 90 during the actuation of the actuating button 70, namely at an inlet valve lip 92 of the inlet valve 18. In the case of reduced pressure in the adjoining pump chamber 20, the liquid can thus flow into the pump chamber 20. The pump chamber 20 is bounded by the valve component 90, an annular housing section 36 of the first housing component 30, and the internally deformable membrane part 60.

If the membrane part is displaced in the direction of the arrow 4 and in the direction of the valve component 90, an elevated pressure is established in the pump chamber, which opens an outlet valve 22 by deflecting the outlet valve lips 94 thereof. The liquid can thus flow into a channel section 24 which is aligned in the main direction of extension 2 and leads as far as the distal end of the first housing component 30. At the distal end of the first housing component 30, two annular lands 32, 34 are provided. The outer land 32 has an internal diameter matched to an annular land 48 of the second housing component 44 in such a way that an interspace defined by the first and second housing components 30, 44 is insulated from the environment. At the annular land 48 of the second housing component 44, an appendage in the form of a lance is provided, which forms an insert 50 that projects into the channel section 24 and predominantly fills a volume thereof. The liquid that has flowed through the channel section 24 of minimized volume as far as the second housing component 44 cannot directly escape here through the delivery opening 28, since the delivery opening 28 has an upstream delivery valve 26 comprising the delivery valve body 96, which is pressed against and hence closes the delivery opening 28 in a sealing manner by the delivery valve spring 98. With rising liquid pressure at the delivery valve 26, however, the delivery valve body 96 is deformed by the force of the delivery valve spring 98 and hence opens the liquid pathway, such that the liquid can escape through the delivery opening 28 under comparatively low pressure and forms a droplet at the droplet formation structure provided beyond the delivery opening 28 in the form of a droplet formation surface 120. Only when this has a volume defined by the geometry of the droplet formation structure does droplet become detached, and hence the droplet can be applied, for example, to an eye, a nostril or an ear of the user.

When the user releases the actuating button 70 after actuation, the actuating button 70 is returned to the starting position thereof by the spring device 72 configured in the manner of a helical metal spring. The membrane part 60 is pulled therewith and the volume of the pump chamber 20 is increased again, such that liquid is sucked from the liquid reservoir 14 into the pump chamber 20. In order to prevent this from giving rise to a reduced pressure in the liquid reservoir 14, the dispenser 10 has a ventilation channel 110 which is provided with a sterile filter 112 and permits flow of further air from an environment into the liquid reservoir 14.

Both the valve component 90 and the membrane part 60 are each configured as a component produced by two-component injection molding. Each component has a rigid component section, namely a securing ring 91, 62, onto each of which is molded a component made of soft plastic. In the case of the enlarged valve component in FIG. 9, the soft plastic especially forms the components already mentioned for the inlet valve lip 92 and the outlet valve lip 94 (which cannot be seen in FIG. 9 owing to the perspective thereof). In the case of the membrane part 60, the constituents produced from soft plastic form a pump chamber wall 64 that points in the direction of the pump chamber 20, and a thicker middle portion that merges into a compensating section 66 and a connecting section 68 on the side remote from the pump chamber 20.

Again with reference to the cross-sectional diagram of FIG. 4, in which the outer button component 76 is absent, it is apparent that the connecting section 68 projects into the button component 80 in a connecting region 70A. The connecting section 60 is secured here by a clamp connection. The clamp connection is elucidated in detail by FIG. 8, which shows a detail of the dispenser with the button component 76 removed. As is apparent here, three apertures 82, 86 are provided in the button component 80. The aperture 82 is the actual coupling aperture. It is configured in the form of an elongate aperture, the opposite longitudinal sides of which form clamp surfaces 84 defining the connecting section. These can be provided with sharp-edged profiling, which press from both sides into the connecting section 68 and hence create the desired firm clamp connection. The apertures 86 aligned in parallel thereto form assembly apertures that serve the purpose of enabling deflection of the lands between the coupling aperture and the assembly apertures during assembly without damage to these lands or other parts of the button component 80.

Likewise referring to FIG. 8, the securing of the button component 80 is elucidated. The button component 80 has two molded-on axis sections 74 that define the rocker axis 6. The axis sections 74 are mounted laterally in bearing loops 40 that are part of the first housing component 30. At the opposite end of the actuating button 70, the actuating button 70 has two similarly configured guide loops 88, into which pins 42 of the first housing component 30 project. This prevents the spring device 72 from pushing the entirety of the button component 80 and the rocker button 70 out of the housing.

As is readily apparent from FIGS. 3 and 4, a connecting region 70A in which the button component 80 is connected to the connecting section 68 of the membrane part 60, and a force input region 70B in which the spring device 72 acts on the button component 76, are separated by different distances from the rocker axis 6. This firstly facilitates the assembly of the individual parts in the limited build space. Secondly, this advantageously allows matching of the design of the dispenser and the return force acting on the actuating button 70.

As can be seen from FIG. 8, the inner button component 80 shown therein is configured with particular regard to technical function thereof in terms of its shape. In order nevertheless to achieve an aesthetically pleasing configuration of the actuating button 70, the second, outer button component 76 is provided, connected to the inner button component 80 by a snap connection. Provided on the outer button component 76 is the pressure surface 78 on which a user places their thumb for the purpose of actuation.

As already elucidated, the dispenser shown is designed as a droplet dispenser. It is designed here such that actuation of the actuating button from an unactuated starting position to the actuated final position brings about the discharge of exactly one droplet. Accordingly, the pump chamber 20 is quite small and has a utilizable pump chamber volume, i.e., a difference between maximum volume and minimum volume of the pump chamber 20, of 40 µl.

The effect of this very small pump volume is that particular precautions have to be taken in order to put the dispenser into operation. As supplied, the dispenser has the pump chamber 20 filled with air. The liquid pathway from the pump chamber 20 to the delivery opening 28 is likewise filled with air.

Figures 5, 6:
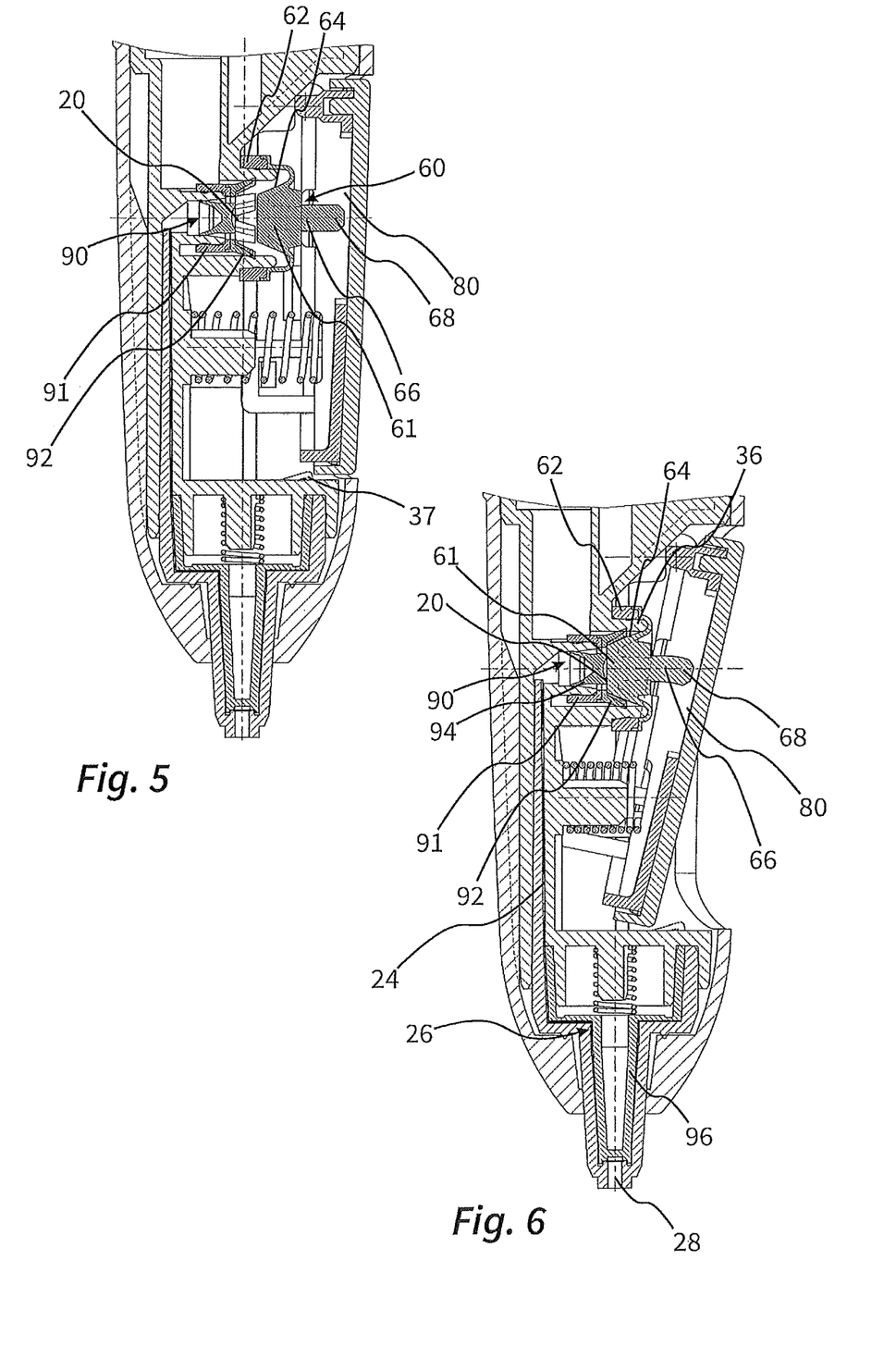
FIGS. 5 and 6 show the operation of actuating the dispenser.

For it to be possible at all, proceeding from this starting state, to displace the air from the pump chamber 20, the pump device 16 has a very small quotient between the minimum volume of the pump chamber 20 in the actuated state and the maximum volume of the pump chamber 20 in the unactuated state. This is illustrated by FIGS. 5 and 6. FIG. 5 shows the unactuated state. FIG. 6 shows the actuated state.

It is apparent that, in the actuated state, the membrane part 60 has been displaced far enough in the direction of the valve component 90 placed onto an annular opposing wall 38 in such a way that the membrane part 60 comes into touch contact therewith. Where the membrane part 60 and the valve component 90 come into touch contact, no residual volume remains between them. It is further apparent that the pump chamber wall 64 which is formed by the membrane part 60, in the transformation to the actuated state, is partly upturned or rolled off, such that, toward the end of the actuation, the pump chamber wall 64 adjoins the annular housing section 36 or only a very narrow gap remains between them. The minimum volume of the pump chamber achievable thereby, which is shown in FIG. 6, is less than 2 µl. The quotient of minimum volume and maximum volume of the pump chamber 20 is thus below 1:20.

It is also apparent from FIGS. 5 and 6 that the rocking mobility of the actuating button has the effect that the connecting section 68 of the membrane part 60 is also correspondingly rocked. In order nevertheless to enable the very small minimum volume of the pump chamber 20, the compensation section 66 is deformed in the manner shown in FIG. 6.

A similar problem to that with the pump chamber 20 is also present with regard to the liquid pathway to the delivery opening 28. Here too, it is advantageous if the volume is at a minimum in order that only little air is present here in the state as supplied, which has to be driven out prior to discharge.

Here, in particular, it is the configuration of the insert 50 that greatly reduces the volume, such that the air driven out from the pump chamber 20 in the direction of the channel section 24, after two to three actuating operations of the actuating button 70, has reached a sufficient pressure to open the delivery valve 26.

Figure 7:
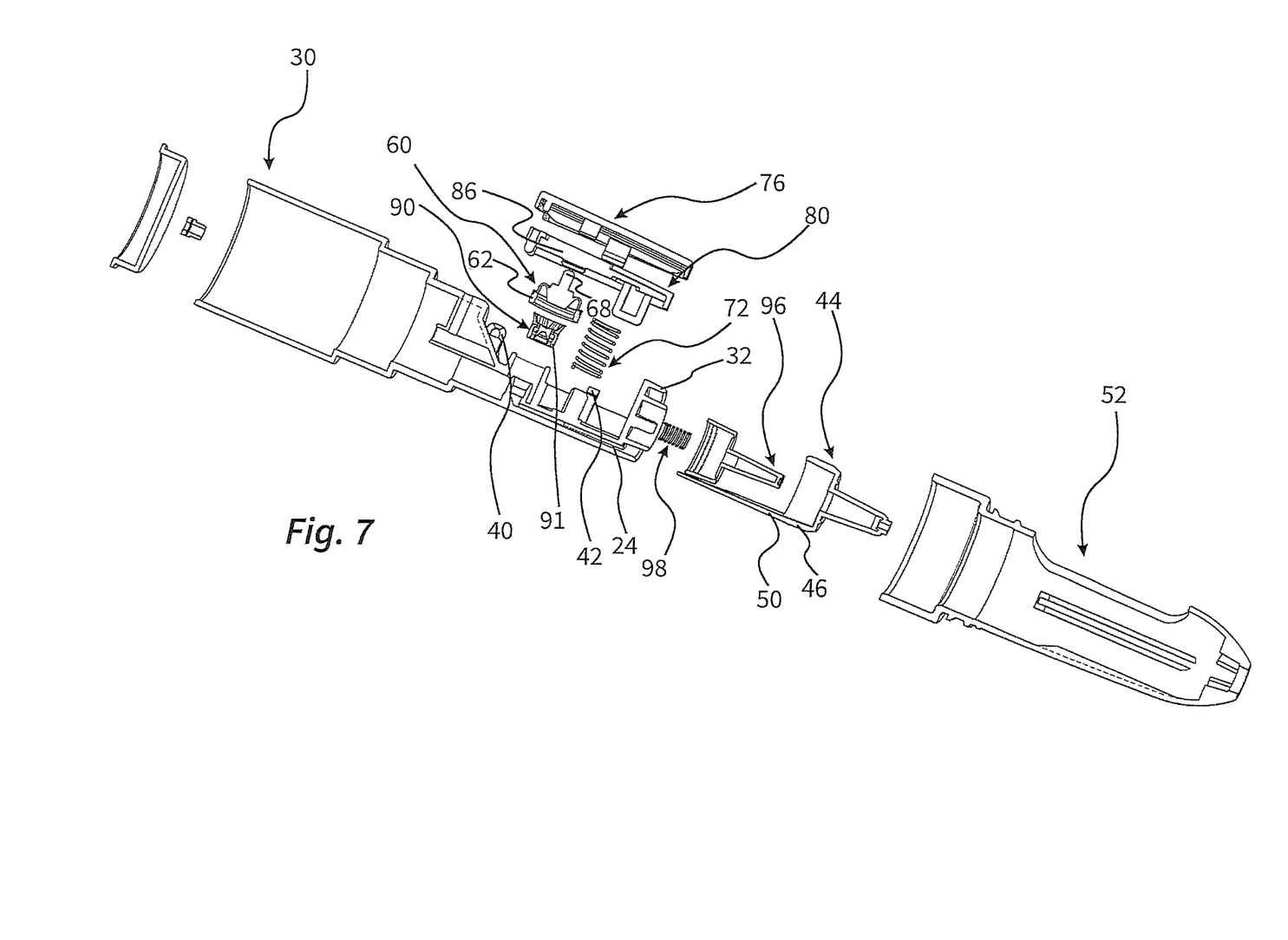
FIG. 7 illustrates the assembly sequence of the individual parts of the dispenser.

The assembly sequence is elucidated hereinafter with reference to FIG. 7.

Also provided in FIGS. 5 and 6, shown by dotted lines, is an optional detent 37 that requires a minimum force on actuation. This is especially appropriate if the dispenser is designed for a pump volume lower than that required for purely gravitational detachment of the droplet. Given such small volumes, the pressure pulse generated by the abrupt pump chamber compression can nevertheless result in detachment of the droplet from the droplet formation surface 120.

Proceeding from the first housing component 30, the valve component 90 is inserted first and secured by the securing ring 91 to the annular opposing wall 38 of the first housing component 30. Subsequently, the return spring 72 and the membrane part 60 are inserted, with the membrane part 60 firmly clamped to the outside of the annular housing section 36 by a securing ring 62, creating a liquid-tight connection.

Subsequently, the internal button component 80 is inserted, which is pressed here into the bearing loops 40 in the region of the axis sections 74 and pushed over the pins 42 provided on the first housing component 30 in the region of the guide loops 88. During the insertion of the button component 80, the coupling aperture 82 is widened by a spreader, such that the connecting section 68 of the membrane part can fit into the coupling aperture without deformation. Subsequently, the spreader is removed, and the clamp connection described is thus created.

Thereafter, a preassembled composite of deformable delivery valve body 96 and second housing component 44 is pushed onto the end face of the first housing component 30, preceded by placement of the delivery valve spring 98 on the end face, and with additional insertion of the insert 50 into the channel section 24 of the first housing component 30.

As the last manufacturing step, the outer housing component 52 is first pushed onto the composite of the preassembled parts, which also achieves securing of the first housing component 30 and the second housing component 44 to one another. Subsequently, the second button component 76 is pressed and snap-fitted onto the first button component 80.

The two latter components 52, 76 have no contact with liquid at all, and therefore do not affect the discharge characteristics of the dispenser. These two components 52, 76 are those components that can be adapted as intended with regard to shape and color, in order to be able to match the dispenser 10 to individual wishes of a manufacturer of pharmaceutical liquids.

Figure 11:
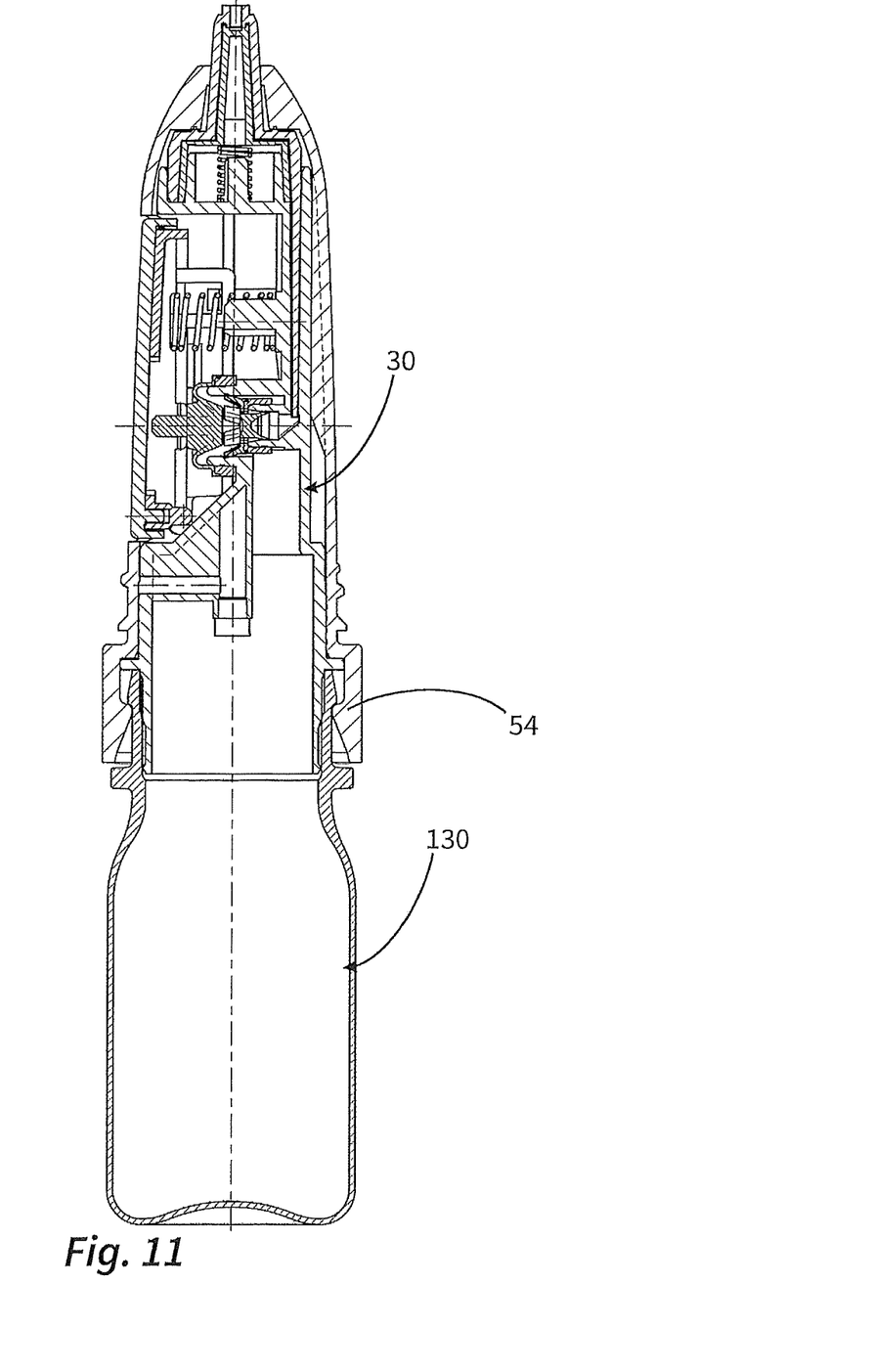
FIG. 11 shows an alternative design of the dispenser.

FIG. 11 shows a second working example of a dispenser of the invention. This has just a single difference from the aforementioned dispenser, namely a configuration of the first housing component 30 and of the outer housing component 52 such that these permit coupling to a separate bottle body 130.

The invention claimed is:

1. A dispenser for discharge of a pharmaceutical liquid, comprising:
a liquid reservoir, a pump device having a volumetrically variable pump chamber, and a delivery opening for delivery of the liquid;
a membrane part that bounds the volumetrically variable pump chamber on one side, the membrane part being comprised at least partly of a soft plastic and altering a volume of the volumetrically variable pump chamber by displacement and/or deformation;
a housing within which the pump device is provided;
an actuating button displaceable relative to the housing between an unactuated starting position and an actuated final position, the actuating button for displacing or deforming the membrane part and for reducing a size of the volumetrically variable pump chamber for discharge of the liquid;
the actuating button having a button component made of a rigid plastic; and
a spring device by which the actuating button is subjected to a force in a direction of the unactuated starting position;
the membrane part being connected to a button component of the actuating button such that the actuating button also moves the membrane part when displaced toward the unactuated starting position;
a connection of the button component to the membrane part being implemented in that a connecting section of the membrane part made of the soft plastic is clamped between at least two clamp surfaces of the button component; and
the button component having a coupling aperture comprising an elongate aperture, at the edge of which the at least two clamp surfaces are provided opposite one another.

2. The dispenser as claimed in claim 1, further including:
at least one elongate assembly aperture provided parallel to the coupling aperture, the at least one elongate assembly aperture enabling deflection of at least one of the at least two clamp surfaces for introducing the connecting section of the membrane part.

3. A dispenser for discharge of a pharmaceutical liquid, comprising:
a liquid reservoir, a pump device having a volumetrically variable pump chamber, and a delivery opening for delivery of the liquid;
a membrane part that bounds the volumetrically variable pump chamber on one side, the membrane part being comprised at least partly of a soft plastic and altering a volume of the volumetrically variable pump chamber by displacement and/or deformation;
a housing within which the pump device is provided;
an actuating button displaceable relative to the housing between an unactuated starting position and an actuated final position, the actuating button for displacing or deforming the membrane part and for reducing a size of the volumetrically variable pump chamber for discharging the liquid discharge;
the dispenser has, on an opposite side of the volumetrically variable pump chamber from the membrane part, an opposing wall into which a valve component of the pump device is inserted, wherein the valve component has at least one valve surface of an inlet valve and/or an outlet valve of the pump device;
the membrane part, in the course of actuation, is displaceable into the volumetrically variable pump chamber in such a way that the membrane part adjoins the valve component at least in sections in an actuated final position;
the valve component having at least one valve lip of the inlet valve or the outlet valve made of elastically deformable plastic; and
the membrane part, during actuation, being displaceable into the volumetrically variable pump chamber in such a way that the membrane part adjoins the valve lip at least in sections in a final actuated position of the membrane part.

4. The dispenser as claimed in claim 3, wherein:
the membrane part has a middle portion that projects into the volumetrically variable pump chamber and has a shape adapted to a shape of the valve component; and/or
the membrane part has a ring surface which surrounds the middle portion of the membrane part and which changes an orientation thereof at least in sections on deformation of the membrane part such that a ring region that points outward in the unactuated starting position points inward in the actuated final position.

5. A dispenser for discharge of a pharmaceutical liquid, comprising:
a liquid reservoir, a pump device having a volumetrically variable pump chamber, and a delivery opening for delivery of the liquid;
a membrane part that bounds the volumetrically variable pump chamber on one side, the membrane part being comprised at least partly of a soft plastic and altering a volume of the volumetrically variable pump chamber by displacement and/or deformation; and
a housing within which the pump device is provided; and
an actuating button displaceable relative to the housing between an unactuated starting position and an actuated final position, the actuating button for displacing or deforming the membrane part and for reducing a size of the volumetrically variable pump chamber for discharging the liquid;
the membrane part being secured circumferentially to a housing section of the housing in an outer edge region; and
the outer edge region of the membrane part being secured to the housing section by a securing ring made of a rigid plastic, wherein the securing ring is formed in one piece with sections of the membrane part from the soft plastic together or is formed as a separate component by which the outer edge region of the membrane part is pressed circumferentially against the housing section.

6. The dispenser as claimed in claim 5, wherein:
the housing section is in annular form, wherein the securing ring is clamped to an outer face of the housing section and wherein an inner face of the housing section forms a circumferential wall of the volumetrically variable pump chamber.

7. A dispenser for discharge of a pharmaceutical liquid, comprising:
a liquid reservoir, a pump device having a volumetrically variable pump chamber, and a delivery opening for delivery of the liquid; and
a membrane part that bounds the volumetrically variable pump chamber on one side, the membrane part being comprised at least partly of a soft plastic and altering a volume of the volumetrically variable pump chamber by displacement and/or deformation;

a housing within which the pump device is provided; and an actuating button displaceable relative to the housing between an unactuated starting position and an actuated final position, the actuating button for displacing or deforming the membrane part and for reducing a size of the volumetrically variable pump chamber for discharging the liquid;

the actuating button comprising a rocker button designed to be rockable with respect to the housing by rocking about a rocker axis;

the rocker button having a rigid button component that presses against the membrane part during rocking movement of the actuating button and hence reduces the volume of the volumetrically variable pump chamber;

the rocker button having a connecting region by which the rocker button presses against the membrane part on actuation; and a spring device that acts on the actuating button in a force input region and which subjects the actuating button to a force in a direction toward the unactuated starting position; and the force input region and the connecting region are provided on the rocker button at different distances from the rocker axis.

8. The dispenser as claimed in claim 7, wherein:

the rocker axis is provided at an opposite end of the rocker button from the delivery opening based on a main direction of extension; and/or a detent is provided on a side of the rocker button remote from the rocker axis and to result in difficulty in depressing the rocker button; and/or an elastically deformable compensation section is provided between the rocker button and a pump chamber wall of the volumetrically variable pump chamber; and/or at least one axis section accommodated in a bearing on a side of the housing is provided on the rocker button.

9. The dispenser as claimed in claim 1, wherein:

the housing has an elongate outer shape based on a main direction of extension, wherein the delivery opening is provided at a distal end of the dispenser; and an actuating button which is provided in a region of an outer surface of the housing at a side of the dispenser can be depressed in a direction of a center axis for deformation of the membrane part of the housing.

10. The dispenser as claimed in claim 1, wherein:

the dispenser is designed as a droplet dispenser and has a droplet formation structure downstream of the delivery opening.

11. The dispenser as claimed in claim 1, further including:

a dispenser cap that can be placed onto the housing and protects the delivery opening when in place.

12. The dispenser as claimed in claim 1, wherein:

a difference between a maximum pump chamber volume and a minimum pump chamber volume is between 20 µl and 50 µl; and/or a quotient between the minimum pump chamber volume and the maximum pump chamber volume is not more than 1:2; and/or a delivery valve is located upstream of the delivery opening; and/or the liquid reservoir has an outer surface in one-piece form together with the housing surrounding the pump device, wherein a separate base is secured to the outer surface at an opposite end from the delivery opening; and/or the liquid reservoir is connected to a surrounding atmosphere by a ventilation channel, or the liquid reservoir has a variable internal volume and is bounded by a flexible or displaceable wall.

13. A dispenser for discharge pharmaceutical liquid, comprising:

a liquid reservoir, a pump device having a volumetrically variable pump chamber, and a delivery opening for delivery of the liquid;

a membrane part that bounds the volumetrically variable pump chamber on one side, the membrane part being comprised at least partly of a soft plastic and altering a volume of the volumetrically variable pump chamber by displacement and/or deformation;

a housing within which the pump device is provided;

an actuating button displaceable relative to the housing between an unactuated starting position and an actuated final position, the actuating button for displacing or deforming the membrane part and for reducing a size of the volumetrically variable pump chamber for discharging the liquid;

the dispenser has, on an opposite side of the volumetrically variable pump chamber from the membrane part, an opposing wall into which a valve component of the pump device is inserted, wherein the valve component has at least one valve surface of an inlet valve and/or an outlet valve of the pump device;

the membrane part, in the course of actuation, is displaceable into the volumetrically variable pump chamber in such a way that the membrane part adjoins the valve component at least in sections in an actuated final position;

wherein the membrane part has a middle portion that projects into the volumetrically variable pump chamber and has a shape adapted to a shape of the valve component, and/or the membrane part has a ring surface which surrounds a middle portion of the membrane part and which changes an orientation thereof at least in sections on deformation of the membrane part such that a ring region that points outward in the unactuated starting position points inward in the actuated final position;

wherein the middle portion has a shape that narrows in a direction of the valve component and the valve component has a complementary goblet-like shape defined by an intake valve lip.

14. The dispenser as claimed in claim 7, wherein the force input region is further removed from the rocker axis than the connecting region, and/or a distance between the rocker axis and the force input region and a distance between the rocker axis and the connecting region differ from one another by at least 20% based on a smaller of the distances.

15. The dispenser as claimed in claim 10, wherein the droplet formation structure comprises a droplet formation surface which surrounds the delivery opening, and/or the dispenser has a coordination between the pump device and the droplet formation structure such that a complete actuation of the actuating button produces exactly one falling droplet.

16. The dispenser as claimed in claim 15, wherein the droplet formation surface is flat or concave and/or is surrounded by a sharp break-off edge.

17. The dispenser as claimed in claim 11, wherein the dispenser cap is configured as a ventilated dispenser cap and has a ventilation opening through which the delivery opening is or can be connected to a surrounding atmosphere even with the dispenser cap in place, and/or the dispenser cap has a pad which, with the dispenser cap in place, is positioned over or on the delivery opening such that any liquid residue that remains downstream of the delivery opening is absorbed and/or decontaminated thereby.

\* \* \* \* \*